(12) United States Patent
Tsai

(10) Patent No.: US 7,645,300 B2
(45) Date of Patent: Jan. 12, 2010

(54) INJECTOR FOR INTRAOCULAR LENS SYSTEM

(75) Inventor: George Tsai, Mission Viejo, CA (US)

(73) Assignee: Visiogen, Inc., Irvine, CA (US)

( * ) Notice: Subject to any disclaimer, the term of this patent is extended or adjusted under 35 U.S.C. 154(b) by 772 days.

(21) Appl. No.: 11/046,154

(22) Filed: Jan. 28, 2005

(65) Prior Publication Data
US 2005/0182419 A1 Aug. 18, 2005

Related U.S. Application Data

(60) Provisional application No. 60/541,429, filed on Feb. 2, 2004.

(51) Int. Cl.
*A61F 2/16* (2006.01)
(52) U.S. Cl. .................................................... 623/6.12
(58) Field of Classification Search ................. 606/107; 623/6.12, 907, 6.32–6.34
See application file for complete search history.

(56) References Cited

U.S. PATENT DOCUMENTS

| | | |
|---|---|---|
| 4,240,163 A | 12/1980 | Galin |
| 4,409,691 A | 10/1983 | Levy |
| 4,636,210 A | 1/1987 | Hoffer |
| 4,655,770 A | 4/1987 | Gupta et al. |
| 4,666,445 A | 5/1987 | Tillay |
| 4,681,102 A | 7/1987 | Bartell |
| 4,702,244 A | 10/1987 | Mazzocco |
| 4,731,079 A | 3/1988 | Stoy |
| 4,790,847 A | 12/1988 | Woods |
| 4,834,094 A | 5/1989 | Patton et al. |
| 4,842,601 A | 6/1989 | Smith |
| 4,862,885 A | 9/1989 | Cumming |
| 4,883,485 A | 11/1989 | Patel |

(Continued)

FOREIGN PATENT DOCUMENTS

DE 19501444 7/1996

(Continued)

OTHER PUBLICATIONS

International Search Report and Written Opinion of the International Searching Authority, mailed May 18, 2005, in related International application No. PCT/US2004/004033.

(Continued)

*Primary Examiner*—William H. Matthews
(74) *Attorney, Agent, or Firm*—Knobbe, Martens, Olson & Bear, LLP.

(57) ABSTRACT

Disclosed is an injector which comprises an injector housing having a longitudinal axis and an injection probe disposed along the longitudinal axis. The injector further comprises an intraocular lens disposed in the housing. The intraocular lens comprises first and second interconnected viewing elements, and the optical axes of the first and second viewing elements are substantially aligned. The optical axes are substantially orthogonal to the longitudinal axis of the housing. The injector further comprises a lens carrier which engages one of the viewing elements. The viewing elements are moveable in response to longitudinal movement of the lens carrier relative to the injector housing. The longitudinal movement causes both (i) the optical axes to be displaced relative to each other and (ii) the viewing elements to be disposed substantially on the longitudinal axis of the injector housing.

18 Claims, 13 Drawing Sheets

U.S. PATENT DOCUMENTS

| | | | |
|---|---|---|---|
| 4,888,012 A | 12/1989 | Horn et al. |
| 4,892,543 A | 1/1990 | Turley |
| 4,919,130 A | 4/1990 | Stoy |
| 4,932,966 A | 6/1990 | Christie et al. |
| 4,963,148 A | 10/1990 | Sule et al. |
| 4,994,082 A | 2/1991 | Richards et al. |
| 5,098,439 A | 3/1992 | Hill |
| 5,123,905 A | 6/1992 | Kelman |
| 5,171,319 A | 12/1992 | Keates et al. |
| 5,190,552 A | 3/1993 | Kelman |
| 5,190,553 A | 3/1993 | Kanert et al. |
| 5,275,604 A | 1/1994 | Rheinish |
| 5,275,623 A | 1/1994 | Sarfarazi |
| 5,326,347 A | 7/1994 | Cumming |
| 5,354,335 A | 10/1994 | Lipshitz et al. |
| 5,425,734 A | 6/1995 | Blake |
| 5,443,506 A | 8/1995 | Garabet |
| 5,468,246 A | 11/1995 | Blake |
| 5,474,562 A | 12/1995 | Orchowski |
| 5,476,514 A | 12/1995 | Cumming |
| 5,494,484 A | 2/1996 | Feingold |
| 5,496,328 A | 3/1996 | Nakajima |
| 5,496,366 A | 3/1996 | Cumming |
| 5,499,987 A | 3/1996 | Feingold |
| 5,507,806 A | 4/1996 | Blake et al. |
| 5,562,731 A | 10/1996 | Cumming |
| 5,578,081 A | 11/1996 | McDonald |
| 5,582,614 A | 12/1996 | Feingold |
| 5,607,472 A | 3/1997 | Thompson |
| 5,616,148 A | 4/1997 | Eagles et al. |
| 5,620,450 A | 4/1997 | Eagles et al. |
| 5,643,275 A | 7/1997 | Blake |
| 5,653,754 A | 8/1997 | Nakajima et al. |
| 5,674,282 A | 10/1997 | Cumming |
| 5,728,102 A | 3/1998 | Feingold |
| 5,772,667 A | 6/1998 | Blake |
| 5,800,442 A | 9/1998 | Wolf et al. |
| 5,807,400 A | 9/1998 | Chambers |
| 5,860,984 A | 1/1999 | Chambers |
| 5,873,879 A | 2/1999 | Figueroa |
| 5,876,440 A | 3/1999 | Feingold |
| 5,921,989 A | 7/1999 | Deacon |
| 5,928,245 A | 7/1999 | Wolf |
| 5,941,886 A | 8/1999 | Feingold |
| 5,944,725 A | 8/1999 | Cicenas et al. |
| 5,947,975 A | 9/1999 | Kikuchi et al. |
| 5,968,094 A | 10/1999 | Werblin et al. |
| 5,984,962 A | 11/1999 | Anello et al. |
| 6,010,510 A * | 1/2000 | Brown et al. ............... 606/107 |
| 6,013,101 A | 1/2000 | Israel |
| 6,106,554 A | 8/2000 | Bretton |
| 6,117,171 A | 9/2000 | Skottun |
| 6,129,733 A | 10/2000 | Brady et al. |
| 6,162,229 A | 12/2000 | Feingold et al. |
| 6,176,878 B1 | 1/2001 | Gwon et al. |
| 6,197,058 B1 | 3/2001 | Portney |
| 6,197,059 B1 | 3/2001 | Cumming |
| 6,203,549 B1 * | 3/2001 | Waldock ................... 606/107 |
| 6,217,612 B1 | 4/2001 | Woods |
| 6,228,094 B1 | 5/2001 | Erdman |
| 6,231,603 B1 | 5/2001 | Lang et al. |
| 6,258,123 B1 | 7/2001 | Young et al. |
| 6,280,471 B1 | 8/2001 | Peyman et al. |
| RE37,387 E | 9/2001 | Brady et al. |
| 6,299,641 B1 | 10/2001 | Woods |
| 6,334,862 B1 | 1/2002 | Vidal et al. |
| 6,406,481 B2 | 6/2002 | Feingold |
| 6,423,094 B1 | 7/2002 | Sarfarazi |
| 6,443,985 B1 | 9/2002 | Woods |
| 6,447,519 B1 | 9/2002 | Brady et al. |
| 6,450,642 B1 | 9/2002 | Jethmalani et al. |
| 6,454,802 B1 | 9/2002 | Bretton et al. |
| 6,464,725 B2 | 10/2002 | Skotton |
| 6,468,282 B2 | 10/2002 | Kikuchi |
| 6,488,708 B2 | 12/2002 | Sarfarazi |
| 6,497,708 B1 | 12/2002 | Cumming |
| 6,503,275 B1 | 1/2003 | Cumming |
| 6,503,276 B2 | 1/2003 | Cumming |
| 6,551,354 B1 | 4/2003 | Ghazizadeh et al. |
| 6,558,420 B2 | 5/2003 | Green |
| 6,761,737 B2 | 7/2004 | Zadno-azizi et al. |
| 6,764,511 B2 | 7/2004 | Zadno-azizi et al. |
| 6,786,934 B2 | 9/2004 | Zadno-azizi et al. |
| 6,818,158 B2 | 11/2004 | Pham et al. |
| 6,846,326 B2 | 1/2005 | Zadno-azizi et al. |
| 6,858,040 B2 | 2/2005 | Nguyen et al. |
| 6,884,261 B2 | 4/2005 | Zadno-Azizi et al. |
| 6,899,732 B2 | 5/2005 | Zadno-Azizi et al. |
| 7,041,134 B2 | 5/2006 | Nguyen et al. |
| 7,097,660 B2 | 8/2006 | Portney |
| 7,125,422 B2 | 10/2006 | Woods et al. |
| 7,198,640 B2 | 4/2007 | Nguyen |
| 7,452,362 B2 | 11/2008 | Zadno-Azizi et al. |
| 2001/0012964 A1 | 8/2001 | Lang et al. |
| 2001/0020171 A1 | 9/2001 | Heyman et al. |
| 2002/0002404 A1 | 1/2002 | Sarfarazi |
| 2002/0004682 A1 | 1/2002 | Zhou et al. |
| 2002/0077633 A1 | 6/2002 | Kikuchi et al. |
| 2002/0082609 A1 | 6/2002 | Green |
| 2002/0107568 A1 | 8/2002 | Zadno-Azizi et al. |
| 2002/0116057 A1 | 8/2002 | Ting et al. |
| 2002/0116061 A1 | 8/2002 | Zadno-Azizi et al. |
| 2002/0138140 A1 | 9/2002 | Hanna |
| 2002/0173847 A1 | 11/2002 | Zadno-Azizi et al. |
| 2002/0188351 A1 | 12/2002 | Laguette |
| 2002/0193876 A1 | 12/2002 | Lang et al. |
| 2003/0018384 A1 | 1/2003 | Valyunin et al. |
| 2003/0074060 A1 | 4/2003 | Zadno-Azizi et al. |
| 2003/0078657 A1 | 4/2003 | Zadno-Azizi et al. |
| 2003/0078658 A1 | 4/2003 | Zadno-azizi |
| 2003/0114927 A1 | 6/2003 | Nagamoto |
| 2003/0187504 A1 | 10/2003 | Weinschenk, III et al. |
| 2004/0160575 A1 | 8/2004 | Ayton et al. |
| 2005/0049700 A1 | 3/2005 | Zadno-Azizi et al. |
| 2005/0165410 A1 | 7/2005 | Zadno-Azizi et al. |
| 2005/0228401 A1 | 10/2005 | Zadno-Azizi et al. |
| 2005/0234547 A1 | 10/2005 | Nguyen et al. |
| 2005/0251236 A1 | 11/2005 | Jeannin et al. |
| 2006/0178741 A1 | 8/2006 | Zadno-Azizi et al. |
| 2006/0184244 A1 | 8/2006 | Nguyen et al. |
| 2006/0259139 A1 | 11/2006 | Zadno-Azizi et al. |
| 2006/0271187 A1 | 11/2006 | Zadno-Azizi et al. |
| 2007/0027540 A1 | 2/2007 | Zadno-Azizi et al. |
| 2007/0032886 A1 | 2/2007 | Tsai et al. |
| 2007/0050025 A1 | 3/2007 | Nguyen et al. |
| 2008/0045971 A1 | 2/2008 | Ayton et al. |

FOREIGN PATENT DOCUMENTS

| | | |
|---|---|---|
| EP | 0162573 | 11/1985 |
| EP | 0337390 A2 | 10/1989 |
| EP | 0336877 | 10/1993 |
| FR | 2784575 | 4/2000 |
| JP | 02-126847 | 5/1990 |
| WO | WO 9513022 | 5/1995 |
| WO | WO 99/20206 | 4/1999 |
| WO | WO 00/21467 | 4/2000 |
| WO | WO 00/27315 | 5/2000 |
| WO | WO 00/61036 | 10/2000 |
| WO | WO 00/66037 | 11/2000 |
| WO | WO 01/19289 | 3/2001 |
| WO | WO 01/34067 | 5/2001 |
| WO | WO 01/64136 | 9/2001 |
| WO | WO 01/66042 | 9/2001 |

| WO | WO 03/015657 | 2/2003 |
| WO | WO 04/000171 | 12/2003 |
| WO | WO 2004/073560 | 9/2004 |

OTHER PUBLICATIONS

International Search Report and Written Opinion of the International Searching Authority, mailed Jan. 18, 2006, in related International application No. PCT/US2005/002871.

U.S. Appl. No. 11/564,482, filed Nov. 29, 2006, our reference.

Hara, "Accommodative Intraocular Lens With Spring Action Part 1. Design and Placement in an Excised Animal Eye," Ophthalmic Surgery, Feb. 1990.

U.S. Appl. No. 10/985,854, Nov. 10, 2004, Method of Implanting an Intraocular Lens, Evans et al., Copy enclosed.

U.S. Appl. No. 12/258,339, filed Oct. 24, 2008.

Notice of Allowance dated Jul. 13, 2009 in U.S. Appl. No. 10/637,376, filed Aug. 8, 2003.

Amendment After Allowance dated Sep. 25, 2009 in U.S. Appl. No. 10/637,376, filed Aug. 8, 2003.

Notice of Allowance dated Sep. 2, 2009 in U.S. Appl. No. 11/080,031, filed Mar. 15, 2005.

* cited by examiner

INJECTOR FOR INTRAOCULAR LENS SYSTEM

RELATED APPLICATIONS

This application claims the benefit under 35 U.S.C. § 119(e) of U.S. Provisional Patent Application No. 60/541,429, filed Feb. 2, 2004, titled INJECTOR FOR INTRAOCULAR LENS SYSTEM. The entire contents of the above-mentioned provisional application are hereby incorporated by reference herein and made a part of this specification.

BACKGROUND OF THE INVENTION

1. Field of the Invention

Various embodiments disclosed herein pertain to insertion of intraocular lenses into the eye of a patient, as well as methods and devices for preparing an intraocular lens for insertion, and for achieving the insertion itself.

2. Description of the Related Art

Artificial intraocular lenses are often implanted to replace or supplement the natural crystalline lens. Such a lens may be implanted where the natural lens has developed cataracts or has lost elasticity to create a condition of presbyopia. Implantation devices have been developed to roll or fold an intraocular lens, and/or assist in implanting a rolled or folded lens through a small incision in the patient's eye. However, these known implantation devices suffer from various drawbacks, many of which are addressed by certain embodiments disclosed herein.

SUMMARY OF THE INVENTION

One aspect of the invention is an injector which comprises an injector housing having a longitudinal axis and an injection probe disposed along the longitudinal axis. The injector further comprises an intraocular lens disposed in the housing. The intraocular lens comprises first and second interconnected viewing elements, and the optical axes of the first and second viewing elements are substantially aligned. The optical axes are substantially orthogonal to the longitudinal axis of the housing. The injector further comprises a lens carrier which engages one of the viewing elements. The viewing elements are moveable in response to longitudinal movement of the lens carrier relative to the injector housing. The longitudinal movement causes both (i) the optical axes to be displaced relative to each other and (ii) the viewing elements to be disposed substantially on the longitudinal axis of the injector housing.

Another aspect of the invention is an injector which comprises an injector housing and an intraocular lens disposed within the housing. The intraocular lens has first and second interconnected viewing elements. The injector further comprises a lens carrier. The lens carrier is moveable relative to the injector housing along a continuously longitudinal path from a first position in which (a) the lens carrier engages the intraocular lens and (b) optical axes of the viewing elements are substantially aligned, to a second position in which (a) one of the viewing elements is forward of the other and (b) the viewing elements are at least partially compacted.

Another aspect of the invention is an injector which comprises an injector housing and an intraocular lens disposed within the housing. The intraocular lens has first and second interconnected viewing elements. The injector further comprises a lens carrier which is operable to move the intraocular lens from a home position of the intraocular lens along a continuously longitudinal path. The continuously longitudinal path extends distally from the home position, past a single-element engagement surface located distal of the home position, and between opposed lens-compacting surfaces located distal of the single-element engagement surface.

Another aspect of the invention is a method of preparing for implantation an intraocular lens having first and second interconnected viewing elements. The method comprises advancing the intraocular lens along a continuously longitudinal path such that one of the viewing elements is situated forward of the other and both of the viewing elements are compacted.

Another aspect of the invention is a method of preparing for implantation an intraocular lens having first and second interconnected viewing elements. The method comprises advancing the intraocular lens along a continuously longitudinal path, and causing, via the advancing, both: (a) one of the viewing elements to be situated forward of the other; and (b) both of the viewing elements to be compacted.

Another aspect of the invention is a method of preparing for implantation an intraocular lens having first and second interconnected viewing elements. The method comprises advancing the intraocular lens along a continuously longitudinal path. The method further comprises: while the intraocular lens is being advanced along the continuously longitudinal path, changing the intraocular lens from a first state in which optical axes of the viewing elements are substantially aligned, to a second state in which the optical axes are not substantially aligned. The method further comprises: while the intraocular lens is being advanced along the continuously longitudinal path, compacting the intraocular lens.

Certain objects and advantages of the invention are described herein. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of the embodiments summarized above are intended to be within the scope of the invention herein disclosed. However, despite the foregoing discussion of certain embodiments, only the appended claims (and not the present summary) are intended to define the invention. The summarized embodiments, and other embodiments of the present invention, will become readily apparent to those skilled in the art from the following detailed description of the preferred embodiments having reference to the attached figures, the invention not being limited to any particular embodiment(s) disclosed.

DETAILED DESCRIPTION OF THE PREFERRED EMBODIMENT

Figure 1:
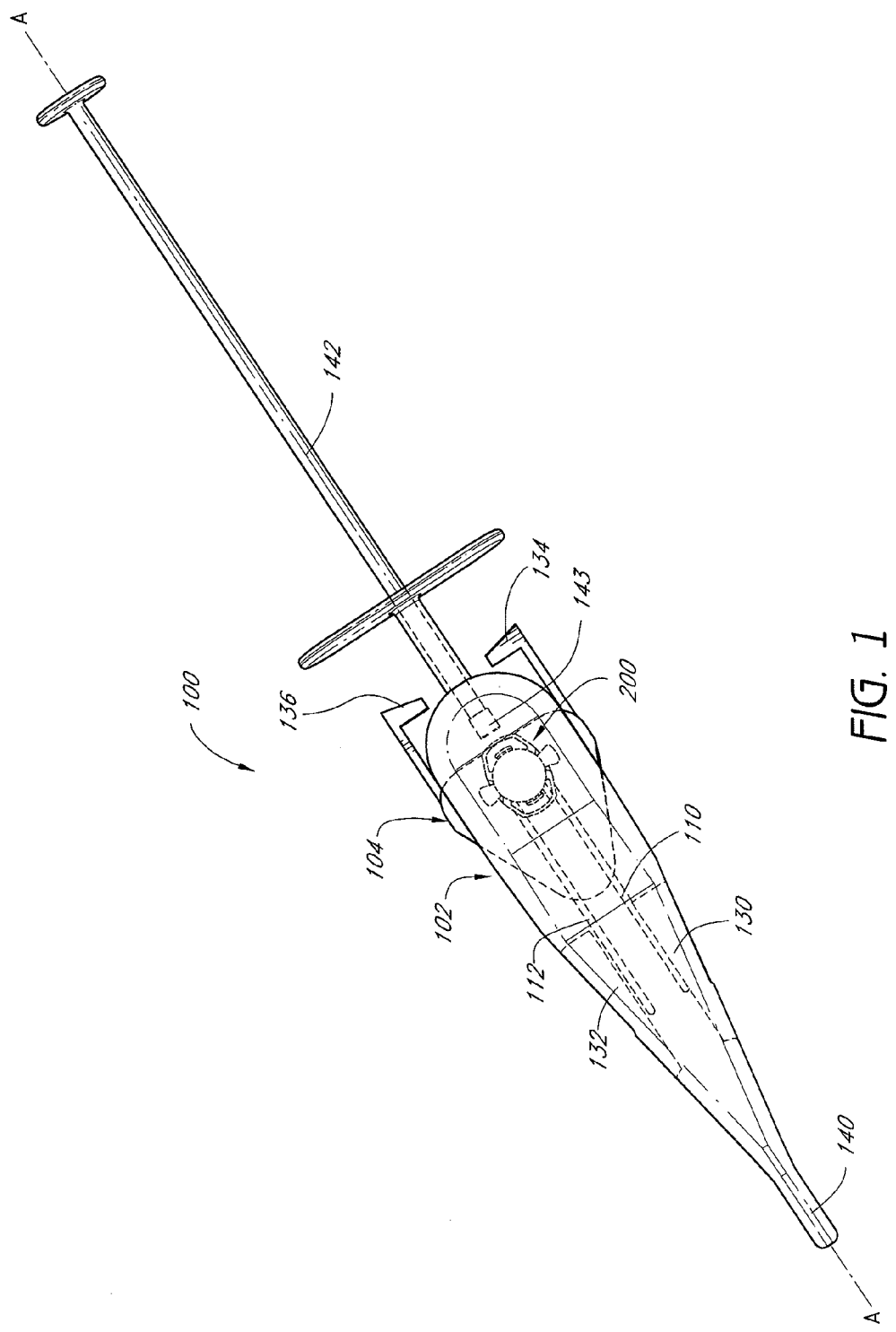
FIG. 1 is a perspective view of one embodiment of an injector for an intraocular lens system.

FIGS. 1-12 depict one embodiment of an injector 100 for injecting an intraocular lens 200 into the eye of a patient. In one embodiment, the intraocular lens 200 comprises an accommodating intraocular lens having two or more interconnected viewing elements or two or more interconnected optics. One, both or all of the viewing elements of the lens 200 may comprise an optic or lens having refractive (or diffractive) power. Alternatively, one, both or all of the viewing elements may comprise an optic with a surrounding or partially surrounding perimeter frame member or members, with some or all of the interconnecting members attached to the frame member(s). As a further alternative, one of the viewing elements may comprise a perimeter frame with an open/empty central portion or void located on the optical axis, or a perimeter frame member or members with a zero-power lens or transparent member therein. In still further variations, one of the viewing elements may comprise only a zero-power lens or transparent member.

In another embodiment, the intraocular lens 200 may comprise any of the various embodiments of accommodating intraocular lenses described in U.S. Patent Application Publication No. 2003/0078656, published Apr. 23, 2003, titled ACCOMMODATING INTRAOCULAR LENS SYSTEM WITH SEPARATION MEMBER, or any of the various embodiments of accommodating intraocular lenses described in U.S. patent application Ser. No. 10/958,871, filed Oct. 5, 2004, titled INTRAOCULAR LENS. The entire disclosure of the above-mentioned publication and the entire disclosure of the above-mentioned patent application are hereby incorporated by reference herein and made a part of this specification. In still other embodiments, the intraocular lens 200 may comprise a single-optic system, of the accommodating or non-accommodating type.

In one embodiment, where the lens 200 comprises a dual-optic system (or, more generally, a dual-viewing-element system), the injector 100 manipulates the lens 200 in two stages while moving the lens 200 along a single axis, specifically a longitudinal axis A-A of the injector 100. (The longitudinal axis A-A is also referred to herein as an "injection axis" of the injector.) In a first stage of manipulation, the injector 100 displaces first and second optics 202, 204 of the lens 200 into a non-coaxial relation (see FIGS. 2, 6), in which the optical axes B-B, C-C of the first and second optics 202, 204 are displaced relative to each other. Displacing the optics 202, 204 and their respective optical axes in this manner reduces the overall thickness of the lens 200. In a second stage of manipulation, the injector 100 compacts, folds or crushes the (thus-displaced) lens 200 into an injection channel 135 (see FIGS. 3, 4, 8) oriented along the injection axis A-A of the injector 100.

In one embodiment, the first optic 202 comprises an anterior optic and the second optic 204 comprises a posterior optic. The terms "anterior" and "posterior" are derived from the positions preferably assumed by the optics 202, 204 upon implantation of the lens 200 in an eye.

The injector 100 generally comprises a housing 102 and an actuator/lens carrier or "sled" 104 slidably mounted on the housing 100. The lens 200 is (initially) stored in the housing 102 in a home position, in a substantially unstressed storage condition (see FIG. 1; also known as a "neutral" or "packaged" condition). In the storage condition the optics 202, 204 are arranged substantially coaxially, with their respective optical axes B-B, C-C substantially aligned or collinear, and with their optical axes B-B, C-C oriented substantially orthogonal to the longitudinal axis A-A of the injector 100/housing 102. As the user advances the actuator 104 distally or forward along the housing, actuator pins 106, 108 formed on the actuator 104 (see FIG. 7) simultaneously advance forward in slots 110, 112 formed in the bottom of the housing 102. Because the pins 106, 108 protrude through the slots 110, 112 and engage one of the viewing elements of the lens 200, the forward advance of the pins 106, 108 urges the lens 200 forward or distally within the housing, generally along the slots 110, 112 and along the longitudinal axis A-A.

Figure 2:
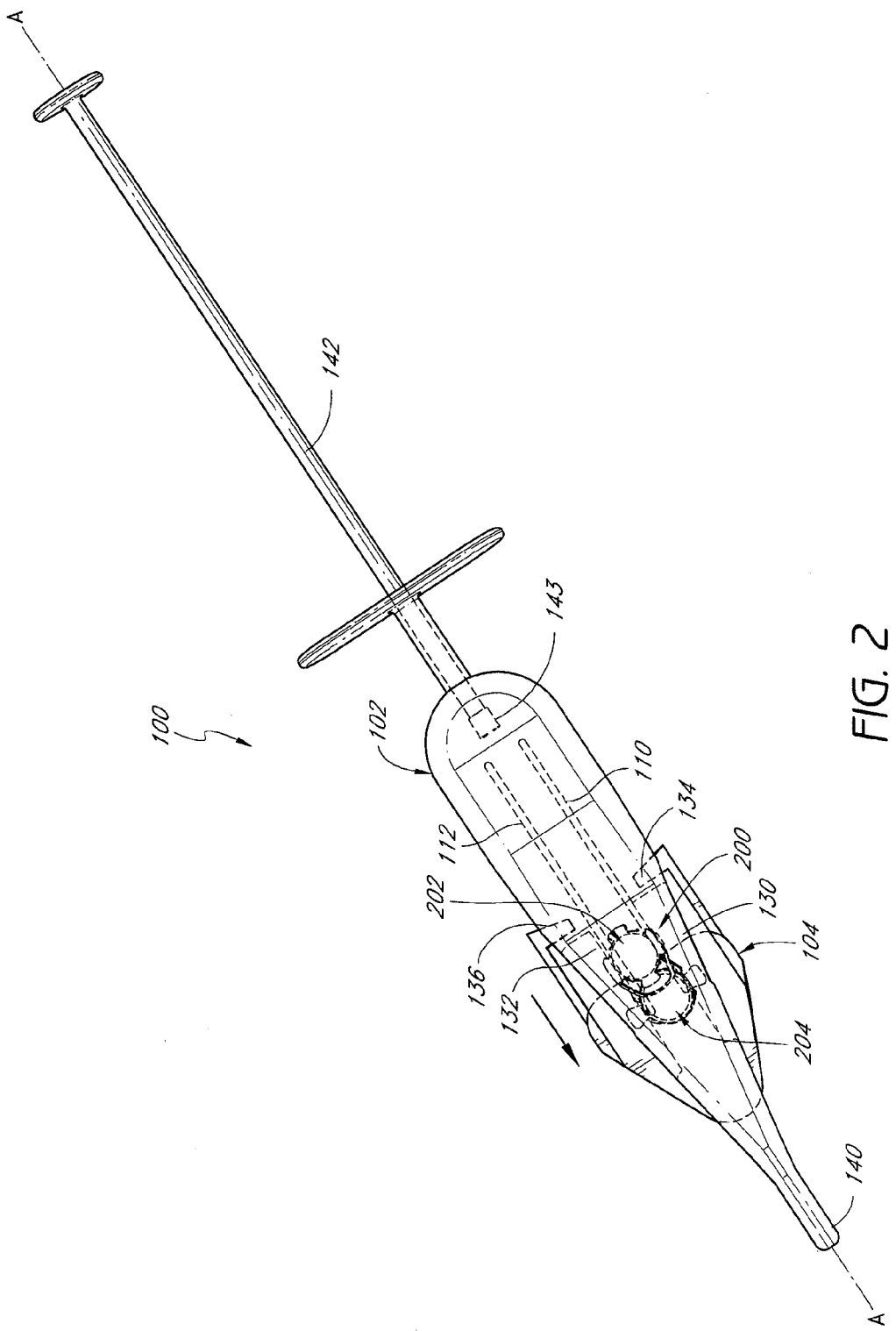
FIG. 2 is a perspective view of the injector of FIG. 1, with the lens system in a displaced condition.
Figure 6:
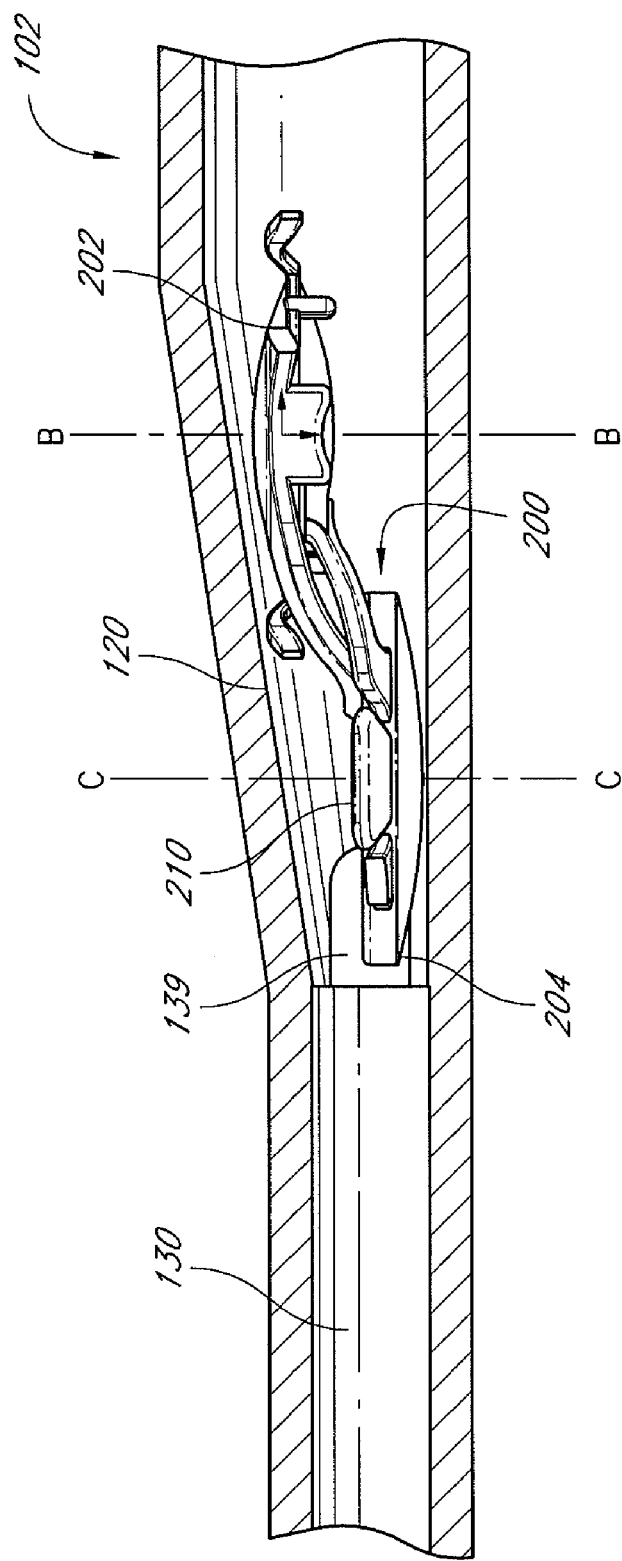
FIG. 6 is a partial side sectional view of a housing of the injector of FIG. 1.
Figure 7:
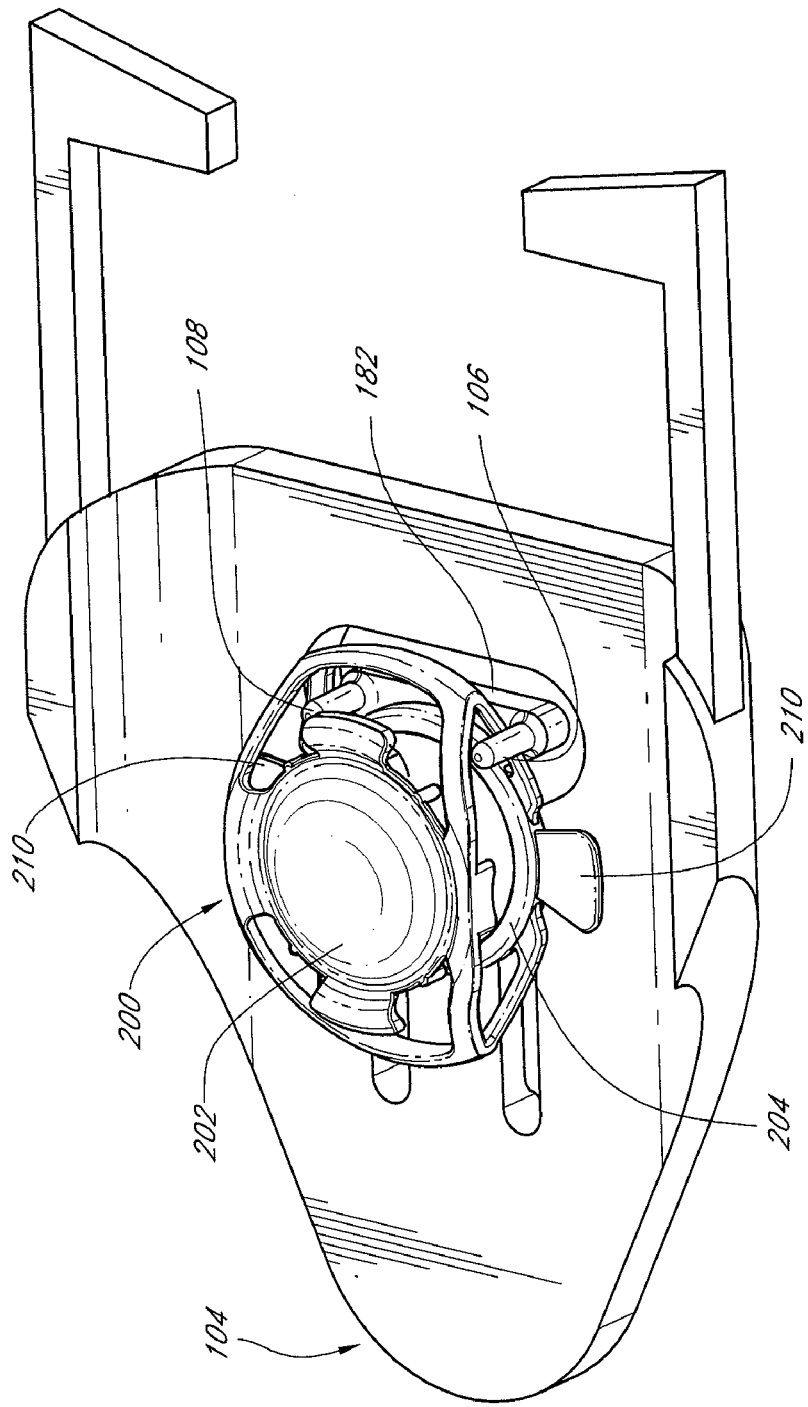
FIG. 7 is a detail perspective view of the actuator and lens system.
Figure 8:
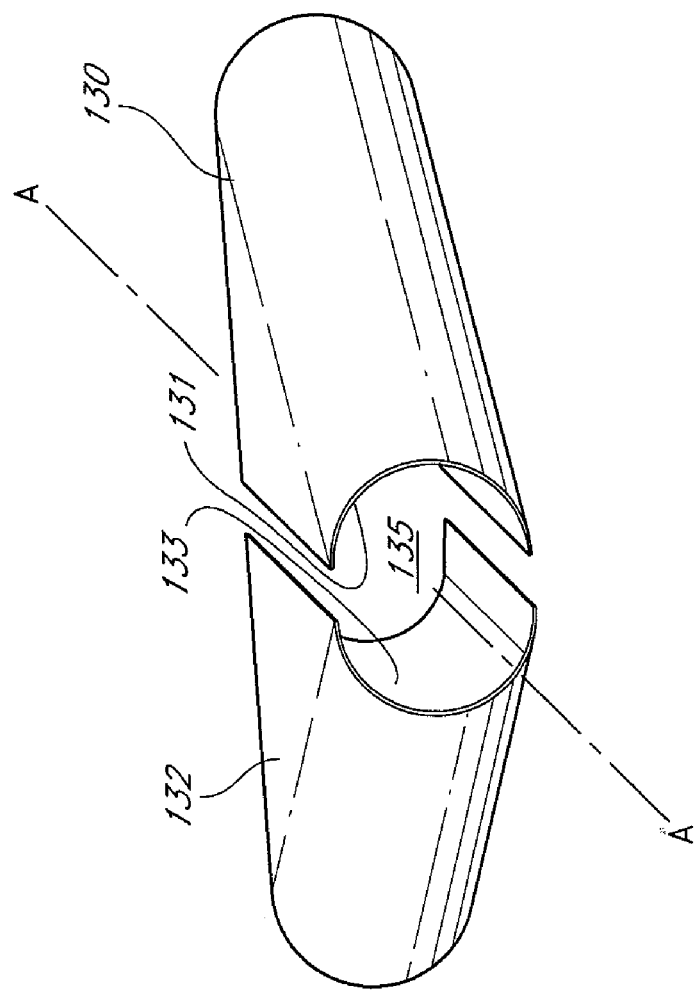
FIG. 8 is a detail perspective view of compacting members of the injector of FIG. 1.

As the lens 200 is advanced forward, the first optic 202 comes into contact with an inclined portion or ramp portion 120 of the housing 102 (see FIG. 6). The inclined portion 120 forces the first optic 202 to move rearward and downward relative to the advancing second optic 204. Thus the first optic 204 falls behind the advancing second optic 204, urging the optics 202, 204 into a flatter, non-coaxial "displaced" condition as shown in FIGS. 2 and 6. As seen in FIG. 2, the optics 202, 204 preferably remain disposed substantially along the longitudinal axis A-A of the injector 100/housing 102 when the lens 200 is in the displaced condition shown in FIGS. 2 and 6. In one embodiment, the optics 202, 204 of the lens 200 are relatively displaced into a condition in which the optics do not "overlap" at all, as viewed along the optical axis of either optic. In still another embodiment, the optics 202, 204 are relatively displaced until the optics 202, 204 are in substantially planar, side-by-side alignment (either overlapping or non-overlapping) such that the thickness of the lens 200 is minimized.

The inclined portion 120 may be considered one type of "single-element engagement surface" as it is one of a variety of suitable structures which may be employed to engage one, but not the other, of the viewing elements of a two-viewing-element lens 200 as the lens 200 advances distally through the injector housing 102.

After the optics 202, 204 have been relatively displaced as shown in FIG. 6, the lens 200 and actuator 104 may be further advanced until the lens 200 is situated between a pair of compacting members or wedge plates 130, 132 (see FIG. 2). Tabs 134, 136 formed on the actuator 104 (and extending through slots 138, 139 formed on the sides of the housing 102, upon sufficient advancement of the actuator 104) engage the compacting members 130, 132 and urge the members 130, 132 forward along with the lens 200 and actuator 104.

As the compacting members 130, 132 move forward, they converge on the lens 200, due to the tapered configuration of the members' outer edges and the housing 102. Each of the compacting members 130, 132 forms a corresponding face 131, 133 in the form of a half-channel on its inner edge (see FIG. 8). Consequently, the converging faces 131, 133 compact, crush and/or fold the lens 200 (which is preferably urged into the "displaced" condition shown in FIGS. 2 and 6 before compacting) in the injection channel 135, which is formed at the meeting of the two members 130, 132 once the members have been driven all the way forward. The injection channel 135 thus formed is substantially aligned on the injection axis A-A with an injection probe or nozzle 140 formed by the housing 102, and a plunger 142. This injection channel 135, which preferably has a cross-section which substantially matches that of an inner lumen of the injector probe 140, holds the folded/crushed and displaced lens 200 ready for further distal longitudinal movement into the injector probe 142.

Figure 3:
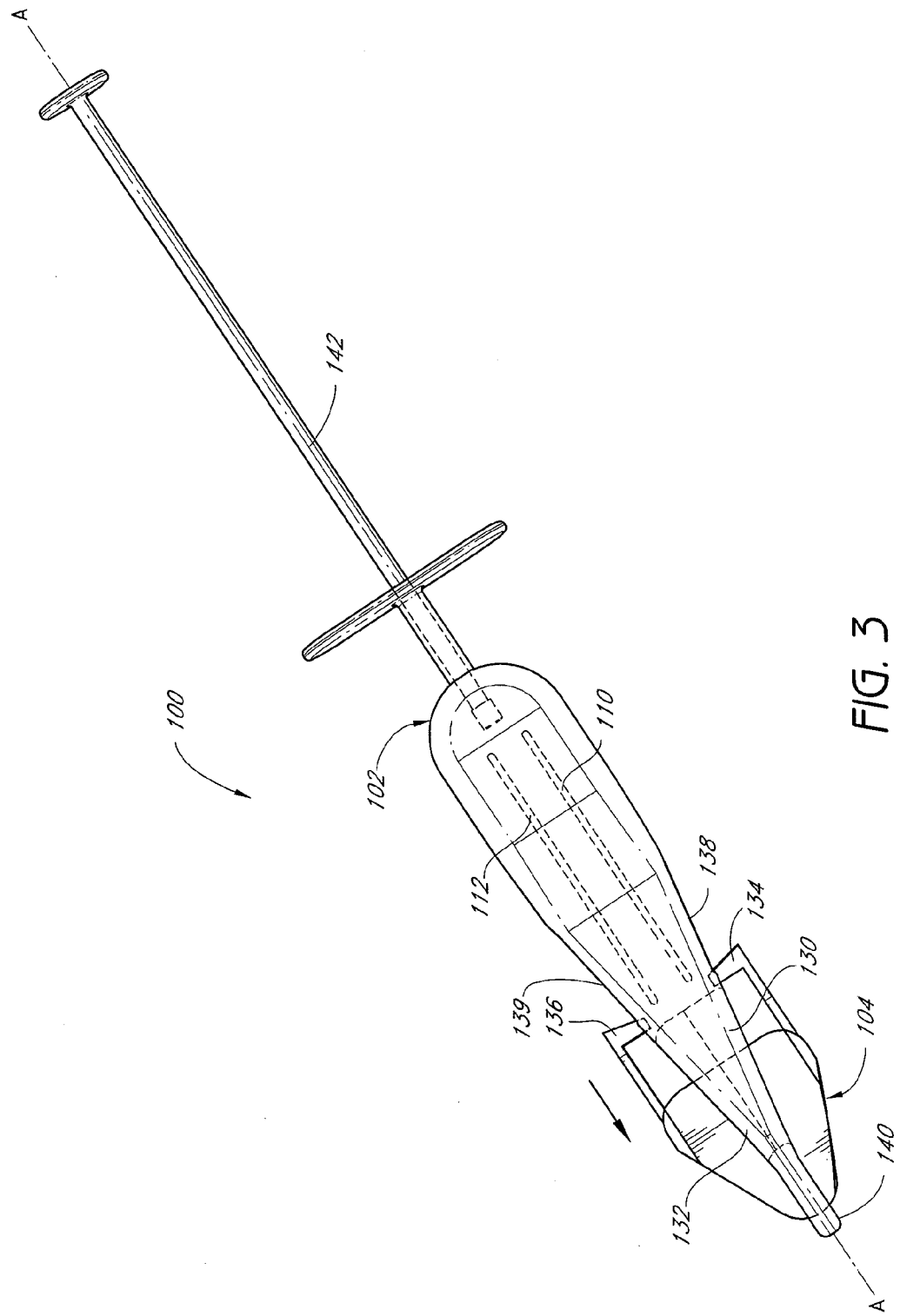
FIG. 3 is a perspective view of the injector of FIG. 1, with the lens system in a displaced and folded/crushed/compacted condition.
Figure 4:
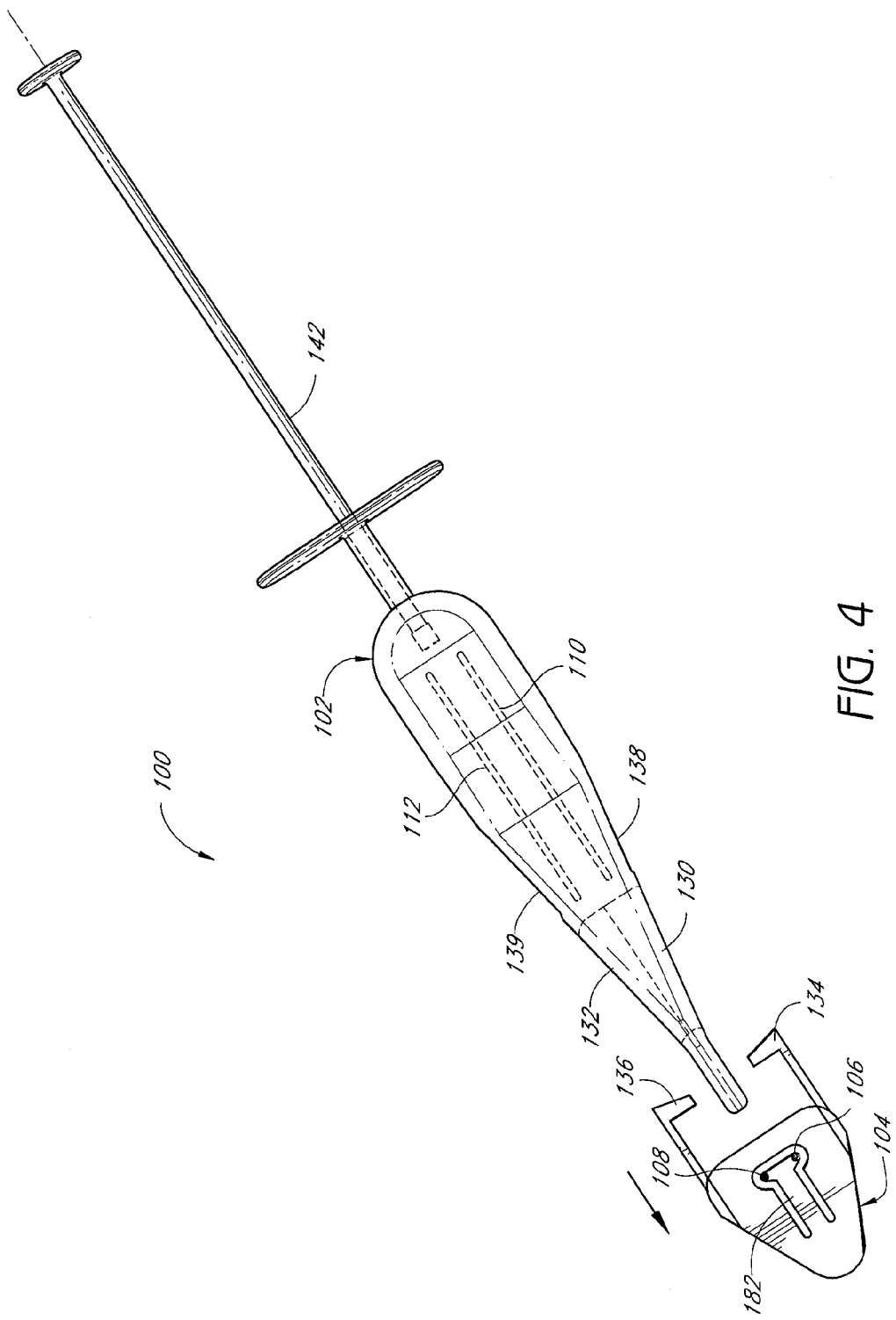
FIG. 4 is a perspective view of the injector of FIG. 1, with the lens system in the displaced and folded/crushed/compacted condition and an actuator thereof removed.

When the compacting members 130, 132 have reached the forwardmost/distalmost position just described and shown in FIG. 3, the members 130, 132 will have converged (and moved laterally) sufficiently for the tabs 134, 136 of the advancing lens carrier 104 to clear and disengage from the rearward surfaces of the members 130, 132. The lens carrier 104 may thus be further advanced distally, detached from the housing 102 and discarded (see FIG. 4).

Figure 9:
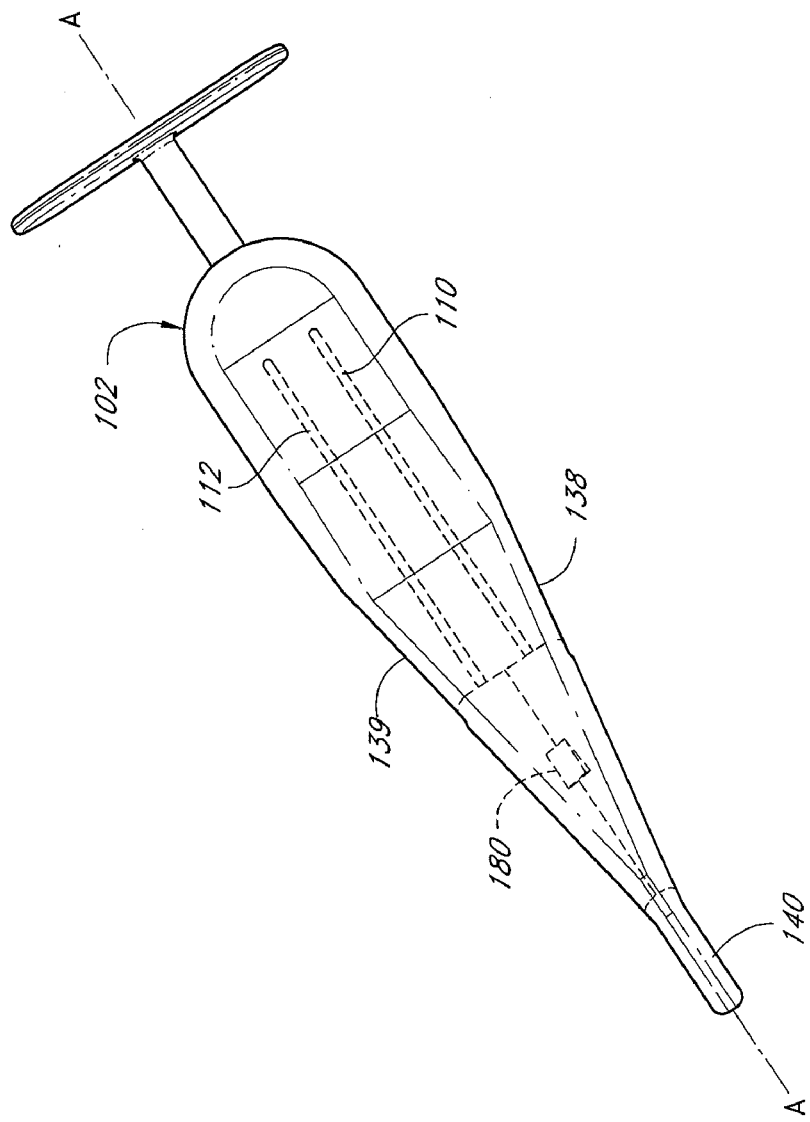
FIG. 9 is a perspective view of the housing.
Figure 11:
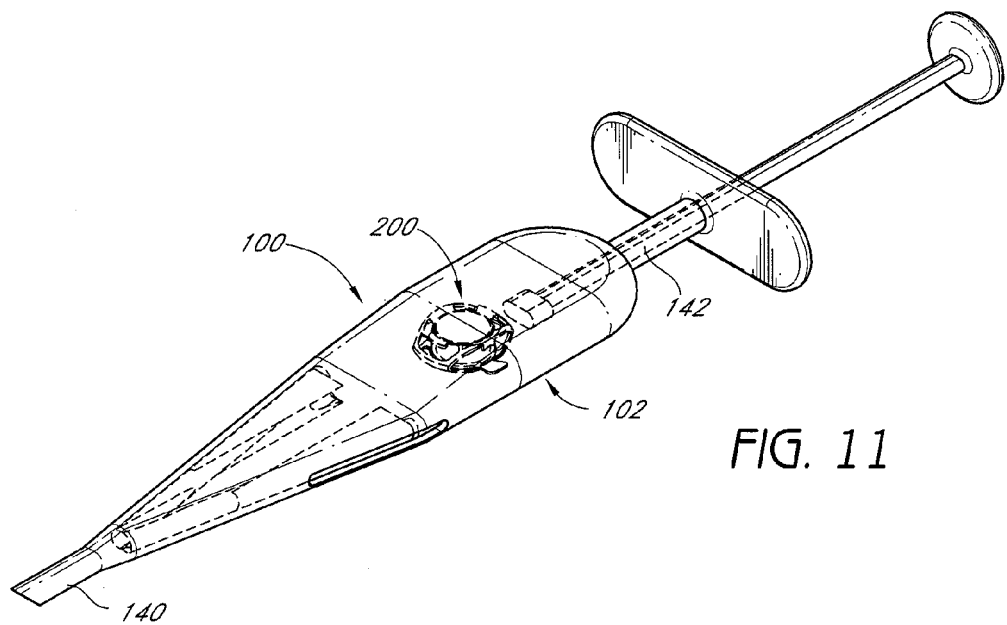
FIG. 11 is a perspective view of the injector.
Figure 10:
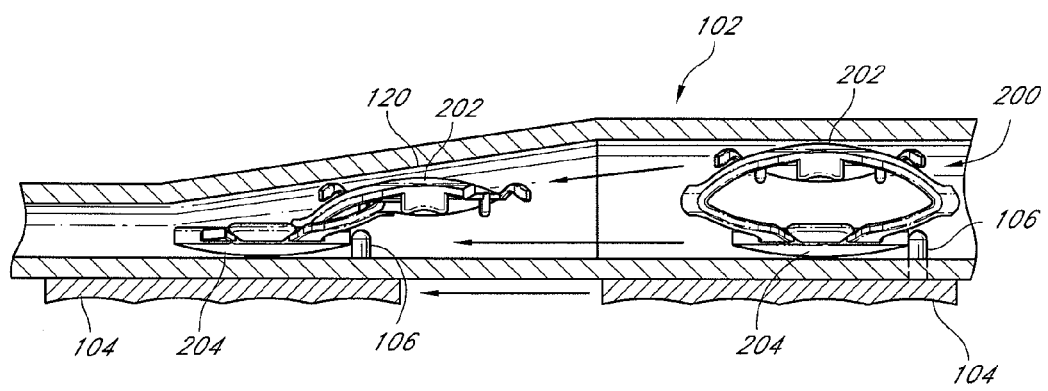
FIG. 10 is a side sectional view of the operation of the actuator.

As seen in FIG. 9, the housing 102 preferably forms a disengagement ramp 180 on its underside. The ramp 180 is positioned to force the pins 106, 108 of the lens carrier 104 to move downward and disengage from the lens 200 (and, if desired, disengage from the slots 110, 112) as the lens 200 moves between the compacting members 130, 132. The lens carrier preferably forms a flexible pin tab 182 (see FIGS. 4, 7) which is configured to contact the ramp 180 upon sufficiently distal movement of the lens carrier 104, and flex downward under the urging of the ramp 180, thus disengaging the pins 106, 108 as discussed above.

Figure 5:
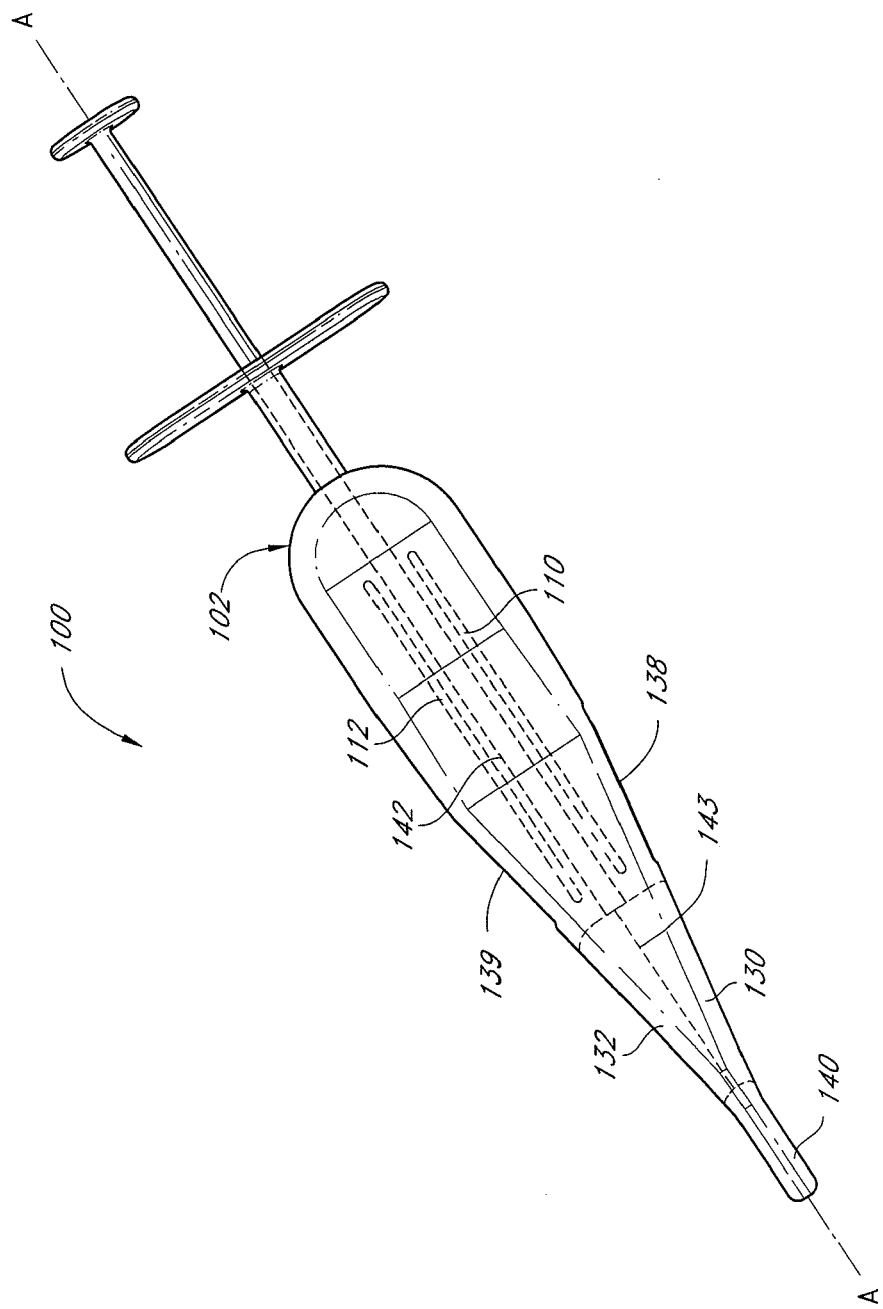
FIG. 5 is a perspective view of the injector of FIG. 1, with the lens system in the displaced and folded/crushed/compacted condition and a plunger thereof advanced forward.

Once the compacting members 130, 132 have folded or compacted the lens 200, application of pressure to the plunger 142 drives the tip 143 of the plunger forward, into the injection channel 135 between the plates 130, 132 and against the "crushed" or "folded" lens 200 disposed therebetween (see FIG. 5). With continued application of pressure, the plunger 142 urges the lens 200 into the inner lumen of the probe 140. The end of the probe 140 may be inserted into the eye of a patient in the typical manner, for delivery of the lens 200 from the tip of the probe.

Figure 12:
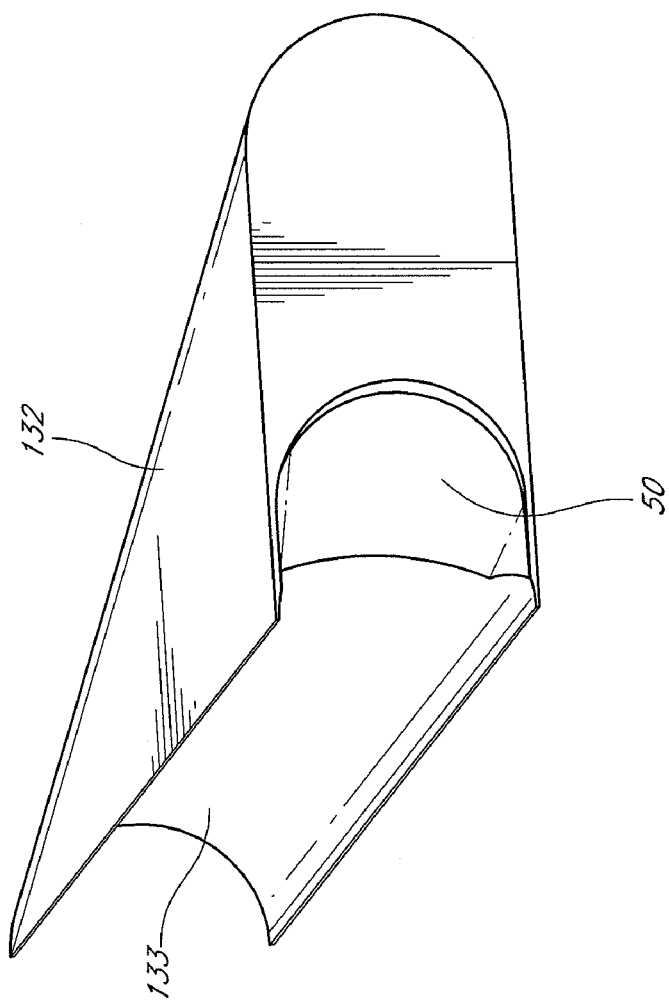
FIG. 12 is a rear detail view of one of the compacting members.

As seen in FIG. 12, each of the compacting members 130, 132 may include a lead-in 150 at the rearward or proximal end of the corresponding face 131, 133 to ensure that the tip 143 of the plunger 142 is easily inserted between the converged compacting members 130, 132.

Figure 13:
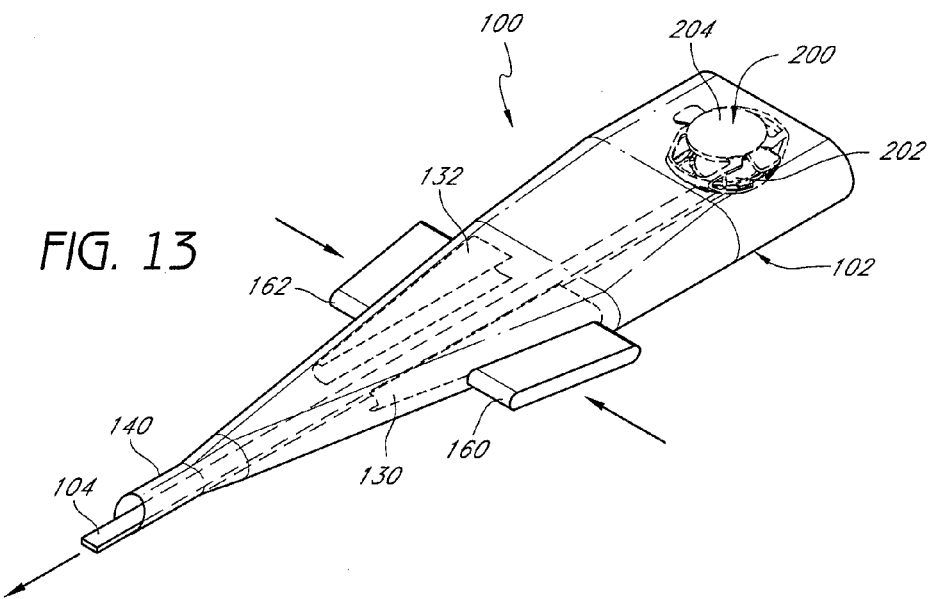
FIG. 13 is a perspective view of another embodiment of the injector.
Figure 14:
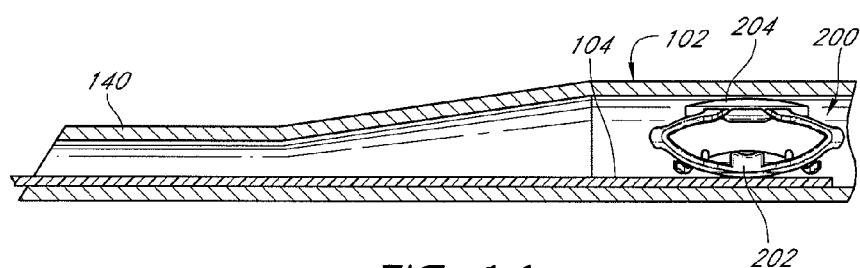
FIG. 14 is a side sectional view of the injector of FIG. 13.
Figure 15:
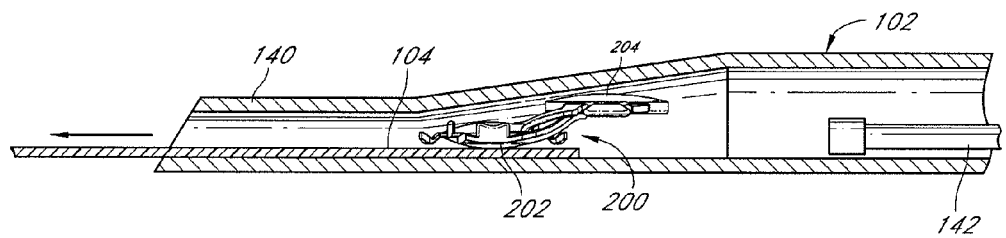
FIG. 15 is another side sectional view of the injector of FIG. 13.

FIGS. 13-15 depict another embodiment of the injector 100, which can be similar to the embodiment of FIGS. 1-12, except as further described and depicted herein. In this embodiment, the actuator/lens carrier 104 may comprise a thin elongate member or strip formed from a suitable polymer film (e.g., PET film). When the lens 200 is in the storage position (see FIG. 14), the first optic 202 rests on the actuator 104, and the second optic 204 is in contact with the adjacent wall of the housing 102. The actuator 104 is then drawn forward through the tip of the probe 140, and the actuator in turn pulls the lens 200 forward, causing displacement of the optics into a non-coaxial condition as described above (see FIG. 15). Once the lens 200 has been drawn between the compacting members 130, 132, the members may be converged by applying pressure to handles 160, 162 formed thereon. (Accordingly, the handles 160, 162 comprise an alternative (or supplement) to the actuator tabs 134, 136 discussed above.) With the lens 200 fully compacted, the plunger 142 may be employed in the usual manner, to push the lens through the injection channel 135 and out the tip of the probe 140.

Accordingly, in the embodiments of FIGS. 1-12 and 13-15, both the lens carrier 104 and the lens 200 are moved longitudinally, along a continuously longitudinal path, from a first or home position (FIG. 1) in which the lens carrier 104 engages the lens 200 and the optical axes B-B, C-C of the viewing elements or optics 202, 204 are substantially aligned, to a second position (FIG. 3) in which one of the viewing elements/optics is forward of the other and the viewing elements/optics are at least partially compacted. The continuously longitudinal path is, in these embodiments, generally coincident with the longitudinal axis or injection axis A-A. The continuously longitudinal path extends distally from the home position, past the single-element engagement surface 120 located distal of the home position, and between the opposed lens-compacting surfaces of the compacting members 130, 132, which are located distal of the single-element engagement surface 120.

The lens carrier 104 and the lens 200 are moved further longitudinally, along the continuously longitudinal path, from the second position to a third position in which the (displaced and compacted) lens 200 is situated within the injector probe 142. From the third position, the lens 200 is urged longitudinally, along the continuously longitudinal path, out the distal tip of the probe 142.

Figure 16:
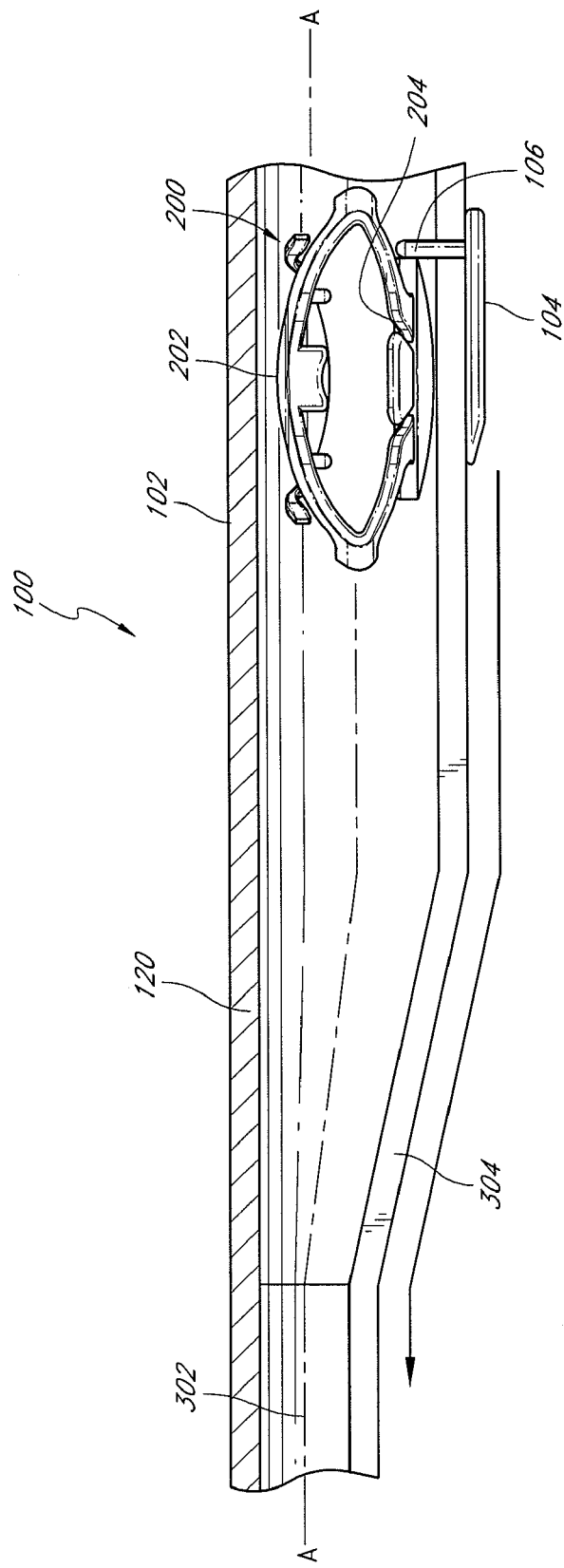
FIG. 16 is a partial side sectional view of another embodiment of the injector.

FIG. 16 depicts another embodiment of the injector 100, which can be similar to the embodiments of FIGS. 1-12 or 13-15, except as further described and depicted herein. In the injector 100 of FIG. 16, the lens 200 is configured to move distally, along a continuously longitudinal path in which only a distal portion 302 thereof is substantially coincident with the longitudinal axis/injection axis A-A. Operation of the lens carrier 104 moves the lens distally and along an upslope 304, whereupon the first optic 202 contacts the single-element engagement surface 120. The surface 120 causes the first optic 202 to fall behind the second optic 204, thus displacing the lens 200 as described and depicted above. Once past the upslope 304, the displaced lens 200 proceeds distally, substantially along the longitudinal axis A-A, until the lens 200 reaches the compacting members (not shown in FIG. 16). The compacting and injection process then continues in the manner described and depicted above.

It is contemplated that the lens 200 may be positioned within (any of the embodiments of) the injector 100 (e.g., with the lens in the storage condition) during manufacture/assembly of the injector. The injector 100, with the lens 200 thus disposed inside, may then be sterilized as a unit, either at the point of manufacture or at some downstream location. Where appropriate, the sterilized injector-lens assembly may be contained in a sterile package, wrapper, bag, envelope, etc. in which the injector-lens assembly may remain until arrival at the point (or time) of use. (The injector-lens assembly may be sterilized before and/or after placement in the package, etc.) This facilitates a simple point-of-use procedure for medical personnel involved in implanting the lens 200 contained in the injector 100: after opening (any) packaging, the physician, or other medical personnel, can compact and insert the lens 200 using the injector 100 as discussed above, without (any need for) removing the lens 200 from the injector 100. Accordingly, there is no need to handle the lens 200 or manually load it into an insertion device at the point of use, both of which can be difficult and tedious, and can compromise the sterility of the lens.

Except as further described herein, any of the embodiments of the injector shown in FIGS. 1-16 may be similar to any of the embodiments of the injector disclosed in U.S. patent application Ser. No. 10/637,376, filed Aug. 8, 2003, titled METHOD AND DEVICE FOR COMPACTING AN INTRAOCULAR LENS. The entire disclosure of the above-mentioned patent application is hereby incorporated by reference herein and made a part of this specification.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular embodiments described above, but should be determined only by a fair reading of the claims that follow.

What is claimed is:

1. A method of preparing for implantation an intraocular lens having first and second interconnected viewing elements placed within an injector having a housing, said method comprising:
   advancing a first actuator to move said intraocular lens continuously along a longitudinal path within the housing and substantially along a longitudinal axis of the housing such that one of said viewing elements is moved forward relative to the other and each of said viewing elements are compacted; and
   advancing a second actuator to move the intraocular lens to a delivery nozzle.

2. The method of claim 1, further comprising advancing the intraocular lens to the delivery nozzle while said intraocular lens is in a compacted state.

3. The method of claim 2, comprising advancing said intraocular lens through the delivery nozzle along said continuously longitudinal path.

4. The method of claim 1, comprising continuously advancing said viewing elements while situating one of said viewing elements forward of the other and compacting both of said viewing elements.

5. The method of claim 1, comprising engaging one of said viewing elements of said intraocular lens with at least one pin.

6. The method of claim 1, further comprising moving compacting members relative to said housing of the injector both longitudinally and laterally to at least partially compact each of said viewing elements.

7. The method of claim 1, wherein said intraocular lens is advanced along said continuously longitudinal path such that both of said viewing elements are laterally compacted.

8. A method of preparing for implantation an intraocular lens having first and second interconnected viewing elements placed within an injector having a housing, said method comprising:
   advancing said intraocular lens along a continuously longitudinal path and not laterally within the housing; and
   causing, via said advancing, both:
      (a) one of said viewing elements to be situated forward of the other; and
      (b) each of said viewing elements to be compacted; and
   advancing compacting members in directions that are both longitudinal and lateral relative to the housing of the injector to at least partially compact both of said viewing elements.

9. The method of claim 8, comprising both at least partially compacting said viewing elements and moving one of said viewing elements forward relative to the other of said viewing element while continuously advancing said intraocular lens.

10. The method of claim 8, comprising engaging one of said viewing elements of said intraocular lens with at least one pin.

11. The method of claim 8, comprising advancing said intraocular lens into the delivery nozzle along said continuously longitudinal path.

12. The method of claim 8, wherein said intraocular lens is advanced along said continuously longitudinal path causing, via said advancing, both of said viewing elements to be laterally compacted.

13. The method of claim 8, wherein said intraocular lens is advanced along said continuously longitudinal path causing, via said advancing, one of said viewing elements to move forward relative to the other.

14. A method of preparing for implantation an intraocular lens having first and second interconnected viewing elements placed within an injector having a housing, said method comprising:
   advancing said intraocular lens along a continuously longitudinal path within the housing;
   while said intraocular lens is being advanced along said continuously longitudinal path, advancing at least one pin to engage and change said intraocular lens from a first state in which optical axes of said viewing elements are substantially aligned, to a second state in which said optical axes are not substantially aligned; and
   while said intraocular lens is being advanced along said continuously longitudinal path, compacting said intraocular lens;
   wherein said at least one pin is elongate and extends in a direction that is substantially perpendicular to the continuously longitudinal path.

15. The method of claim 14, comprising advancing said intraocular lens along an injection axis from said first state to said second state.

16. The method of claim 15, comprising advancing said intraocular lens into the delivery nozzle.

17. The method of claim 14, wherein said intraocular lens is laterally compacted while said intraocular lens is being advanced along said continuously longitudinal path.

18. The method of claim 14, wherein one of said optical axes is positioned forward of the other in the second state.

* * * * *

UNITED STATES PATENT AND TRADEMARK OFFICE
CERTIFICATE OF CORRECTION

| | | |
|---|---|---|
| PATENT NO. | : 7,645,300 B2 | Page 1 of 1 |
| APPLICATION NO. | : 11/046154 | |
| DATED | : January 12, 2010 | |
| INVENTOR(S) | : George Tsai | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1258 days.

Signed and Sealed this

Twenty-first Day of December, 2010

David J. Kappos
*Director of the United States Patent and Trademark Office*